(12) United States Patent
Lin et al.

(10) Patent No.: US 9,927,363 B2
(45) Date of Patent: Mar. 27, 2018

(54) REAL-TIME BASELINE CORRECTION TECHNIQUE FOR INFRARED TIME-RESOLVED PHOTOLUMINESCENCE

(71) Applicant: ARIZONA BOARD OF REGENTS ON BEHALF OF ARIZONA STATE UNIVERSITY, Tempe, AZ (US)

(72) Inventors: Zhi-Yuan Lin, Tempe, AZ (US); Yong-Hang Zhang, Tempe, AZ (US)

(73) Assignee: Arizona Board of Regents on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 15/080,447

(22) Filed: Mar. 24, 2016

(65) Prior Publication Data

US 2016/0282272 A1    Sep. 29, 2016

Related U.S. Application Data

(60) Provisional application No. 62/137,690, filed on Mar. 24, 2015.

(51) Int. Cl.
  *G01J 5/02*     (2006.01)
  *G01N 21/64*    (2006.01)
  *G01N 21/27*    (2006.01)

(52) U.S. Cl.
  CPC ....... *G01N 21/6489* (2013.01); *G01N 21/274* (2013.01); *G01N 21/6408* (2013.01)

(58) Field of Classification Search
  CPC .......... G01N 21/6489; G01N 21/6408; G01N 21/6458
  See application file for complete search history.

(56) References Cited

U.S. PATENT DOCUMENTS

| | | | | |
|---|---|---|---|---|
| 3,975,098 A | * | 8/1976 | West ..................... | G01J 3/4406 250/363.01 |
| 5,202,744 A | * | 4/1993 | Louis ................. | G01N 21/6408 356/417 |
| 5,459,604 A | * | 10/1995 | Corkum ................ | B82Y 20/00 257/184 |
| 5,938,617 A | * | 8/1999 | Vo-Dinh .............. | A61B 5/0059 436/171 |
| 6,081,127 A | * | 6/2000 | Wagner ............. | G01N 21/6489 324/754.23 |

OTHER PUBLICATIONS

Olsson et al., "Luminescence decay and injected carrier lifetime in the high injection region of AlGaAs lasers," Jun. 1982, IEEE Journal of Quantum Electronics, vol. QE-18, No. 6, pp. 971-976.*
Movtchan et al., "Luminescence from a Si-SiO2 nanocluster-like structure prepared by laser ablation," 1995, Thin Solid Films, vol. 255, pp. 286-289.*
Olsson et al., "Nonlinear luminescence and time-resolved diffusion profiles of photoexcited carriers in semiconductors," 1982, American Institute of Physics, vol. 41, pp. 659-661.*

(Continued)

*Primary Examiner* — Kiho Kim
(74) *Attorney, Agent, or Firm* — Polsinelli PC; Ari M. Bai

(57) ABSTRACT

Systems and methods for a real-time baseline correction technique for infrared time-resolved photoluminescence are disclosed.

19 Claims, 12 Drawing Sheets

(56) References Cited

OTHER PUBLICATIONS

Nakano et al., "In-Situ second-harmonic generation and luminescence measurements for structural characterization of ruthenium-polypyridine complex monolayers with two and four aliphatic at the air/water interface," Journal of Physical Chemistry B, vol. 102, pp. 8569-8573.*

Tada et al., "Optically detected ESR of luminescence centers in a-As2S3," 1984, American Institute of Physics, vol. 20, pp. 326-332.*

Grein, C. H. et al., "Theoretical performance of very long wavelength InAs/In(x)Ga(1-x) superlattice based infrared detectors," Applied Physics Letters 65, 2532 (1994).

Youngdale, E. R. et al., "Recombination lifetime in InAs—Ga1-xInxSb superlattices," Journal of Vacuum Science and Technology B 12, 1129 (1993).

Donetsky, D. et al., "Minority carrier lifetime in type-2 InAs-GaSb strained-layer superlattices and bulk HgCdTe materials," Applied Physics Letters 97, 052108 (2010).

Connelly, B. C. et al., "Direct minority carrier lifetime measurements and recombination mechanisms in long-wave infrared type II superlattices using time-resolved photoluminescence," Applied Physics Letters 97, 251117 (2010).

Steenbergen, E. H. et al., "Significantly improved minority carrier lifetime observed in a long-wavelength infrared III-V type-II superlattice comprised of InAs/InAsSb," Applied Physics Letters 99, 251110 (2011).

Olson, B. V. et al., "Time-resolved optical measurements of minority carrier recombination in a mid-wave infrared InAsSb alloy and InAs/InAsSb superlattice," Applied Physics Letters 101, 092109 (2012).

Höglund, L. et al.., "Minority carrier lifetime in mid-wavelength infrared InAs/InAsSb superlattices: Photon recycling and the role of radiative and Shockley-Read-Hall recombination mechanisms", Apply. Phys. Lett. 105, 193510 (2014).

Höglund, L. et al.., "Influence of carrier concentration on the minority carrier lifetime in mid-wavelength infrared InAs/InAsSb superlattices," Infrared Physics & Technology, 70, 62-65 (2015).

Reisinger, A. R. et al., "Photoluminescence of infrared-sensing material using an FTIR spectrometer," Review of Scientific Instruments 79, 82 (1989).

Lawless, P. A. et al., "Baseline corrector for boxcar integrator instruments and its application to plasma chromatography," Review of Scientific Instruments 48, 240 (1976).

Kaur, M. et al., "Comparison of different approaches for removal of baseline wander from ECG signal," Proceeding of the International Conference and Workshop on Emerging Trends in Technology 3, 1290 (2011).

Kottke, T. et al., "A simple digital method for compensation of baseline drift in low-frequency small-signal waveform measurements," Army Research Laboratory report ARL-MR-446, 1999.

* cited by examiner

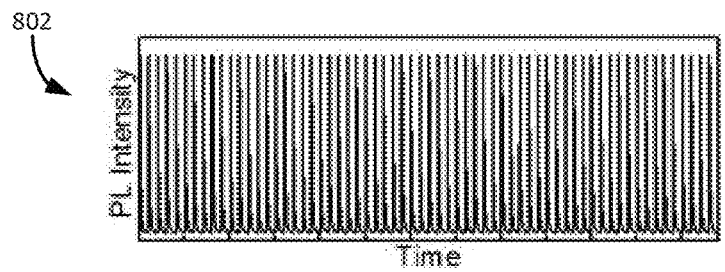
FIG. 8A
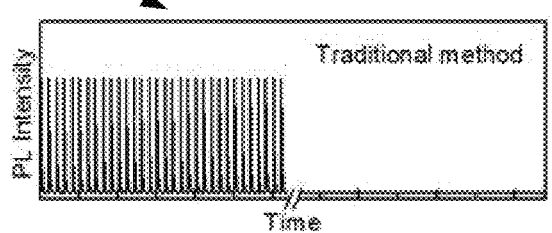
FIG. 8B1
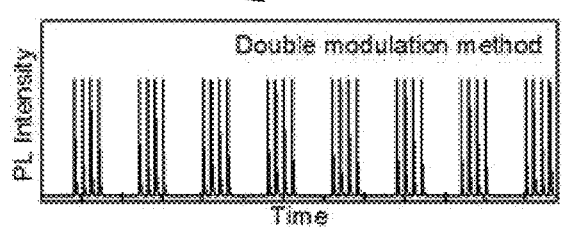
FIG. 8B2
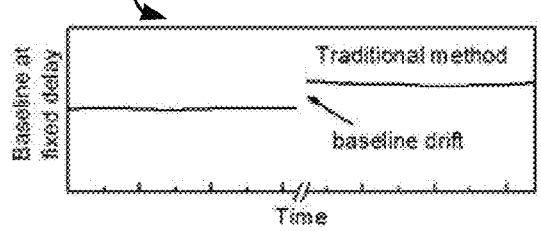
FIG. 8C1
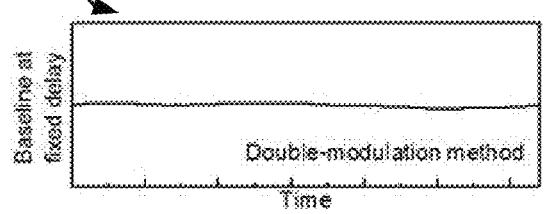
FIG. 8C2
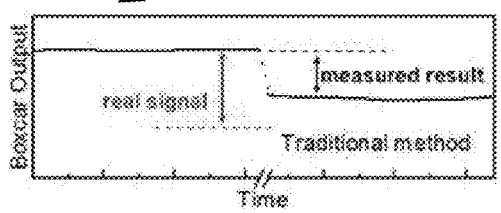
FIG. 8D1
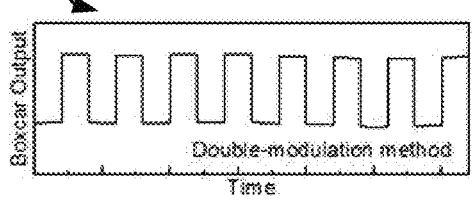
FIG. 8D2

REAL-TIME BASELINE CORRECTION TECHNIQUE FOR INFRARED TIME-RESOLVED PHOTOLUMINESCENCE

CROSS-REFERENCE TO RELATED APPLICATIONS

This is a non-provisional application that claims benefit of U.S. provisional application Ser. No. 62/137,690 filed on Mar. 24, 2015, which is herein incorporated by reference in its entirety.

GOVERNMENT SUPPORT

This invention was made with government support under W911 NF-10-1-0524 awarded by the Army Research Office. The government has certain rights in the invention.

FIELD

The present invention relates to a real-time baseline technique, and in particular to a real-time baseline correction technique for infrared time-resolved photoluminescence.

BACKGROUND

Time-resolved photoluminescence (TRPL) is a powerful tool to characterize the carrier dynamics in semiconductors. In many situations such as in solar cells and photodetectors, the excess carrier decay behavior at low excess carrier densities give more valuable information since it is close to device working condition. However, the photoluminescence (PL) signal is weak from samples with low excess carrier density, and specifically for the infrared regime, the background blackbody radiation contributes significantly to the overall noise. While approaches such as improving the light collecting efficiency or increasing the detector effective area can increase the collected signal intensity, the former needs complicated optical system design and the latter sacrifices the system band width due to larger parasitic capacitance. A long integration time is therefore required to suppress the noise and achieve a proper signal-to-noise ratio for TRPL measurements.

BRIEF DESCRIPTION OF THE DRAWINGS

FIGS. 8A, 8B1, 8B2, 8C1, 8C2, 8D1 and 8D2 are schematic comparisons between the signals in the traditional method and the real-time baseline correction method;

Corresponding reference characters indicate corresponding elements among the view of the drawings. The headings used in the figures do not limit the scope of the claims.

DETAILED DESCRIPTION

Figure 1:
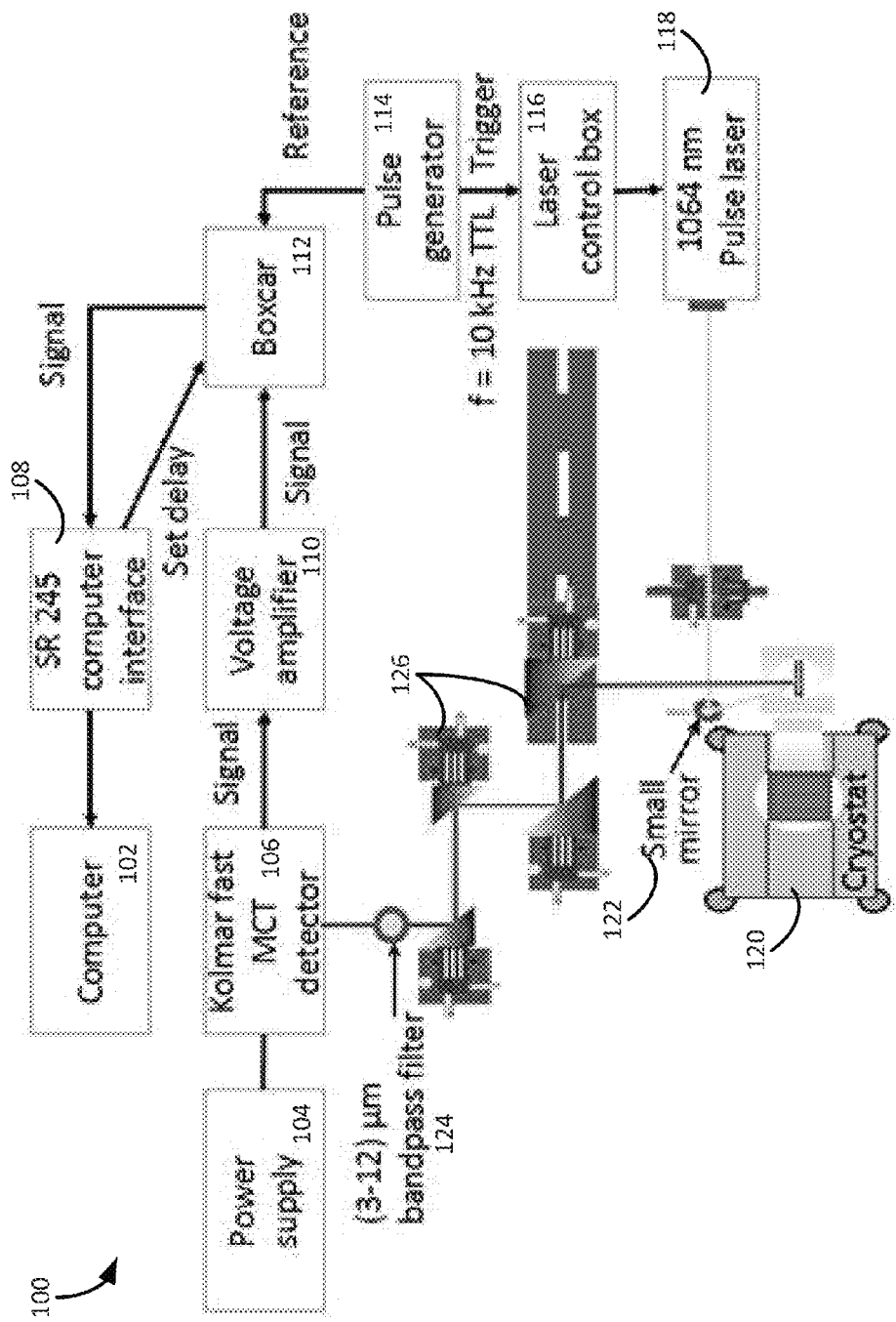
FIG. 1 is a simplified illustration showing a traditional time-resolve PL ("TRPL") measurement setup.

Aspects of the present disclosure involve systems, methods, computer program products, and the like for a real-time baseline correction (RBC) method for time-resolved photoluminescence (TRPL) that is similar in principle with real-time baseline correction technique in Fourier transform infrared spectroscopy (FTIR). The RBC method utilizes affordable equipment such as boxcar, lock-in amplifier and chopper to measure the TRPL signal. As an inexpensive instrument, a boxcar averager is capable of recovering the transient photoluminescence signal. The RBC method significantly suppresses the noise, and therefore is capable of measurement with higher signal-to-noise-ratio compared with the traditional boxcar-based TRPL experiment.

Referring to the drawings, embodiments of a real-time baseline correction technique for infrared time-resolved photoluminescence are illustrated in FIGS. 3-13.

2.1 Experimental Methodology

The details about experimental setups and procedures of the one particular method and a novel real-time baseline correction method for TRPL measurements will be discussed in this section.

One particular system 100 for obtaining TRPL measurements is shown in FIG. 1. In general, the PL sample is mounted inside a cryostat 120 for low temperature measurements, and is excited by a Wedge XF 1064 nm pulse laser 118. The laser 118 has, in one particular embodiment, a pulse width smaller than 1 ns, with a pulse energy adjustable from 7 µJ to 70 µJ, and a frequency adjustable from 10 kHz to 100 kHz. The PL is then directed by parabolic mirrors 126 into a Kolmar KV-104 fast MCT detector 106 with a bandwidth from DC to 50 MHz. The detector output voltage is amplified utilizing a voltage amplifier 110 before it goes into a boxcar integrator or device 112, which is a sampling instrument that integrates the applied input signal during a predefined gate width, starting at a delay after an applied trigger. The boxcar 112 is synchronized with the pulse laser by a 10 kHz Transistor-Transistor Logic (TTL) square wave generated by a pulse generator 114. A computer 102 communicates with the boxcar 112 via a Stanford SR 245 computer interface 108 to set a delay of the boxcar device.

Figure 2:
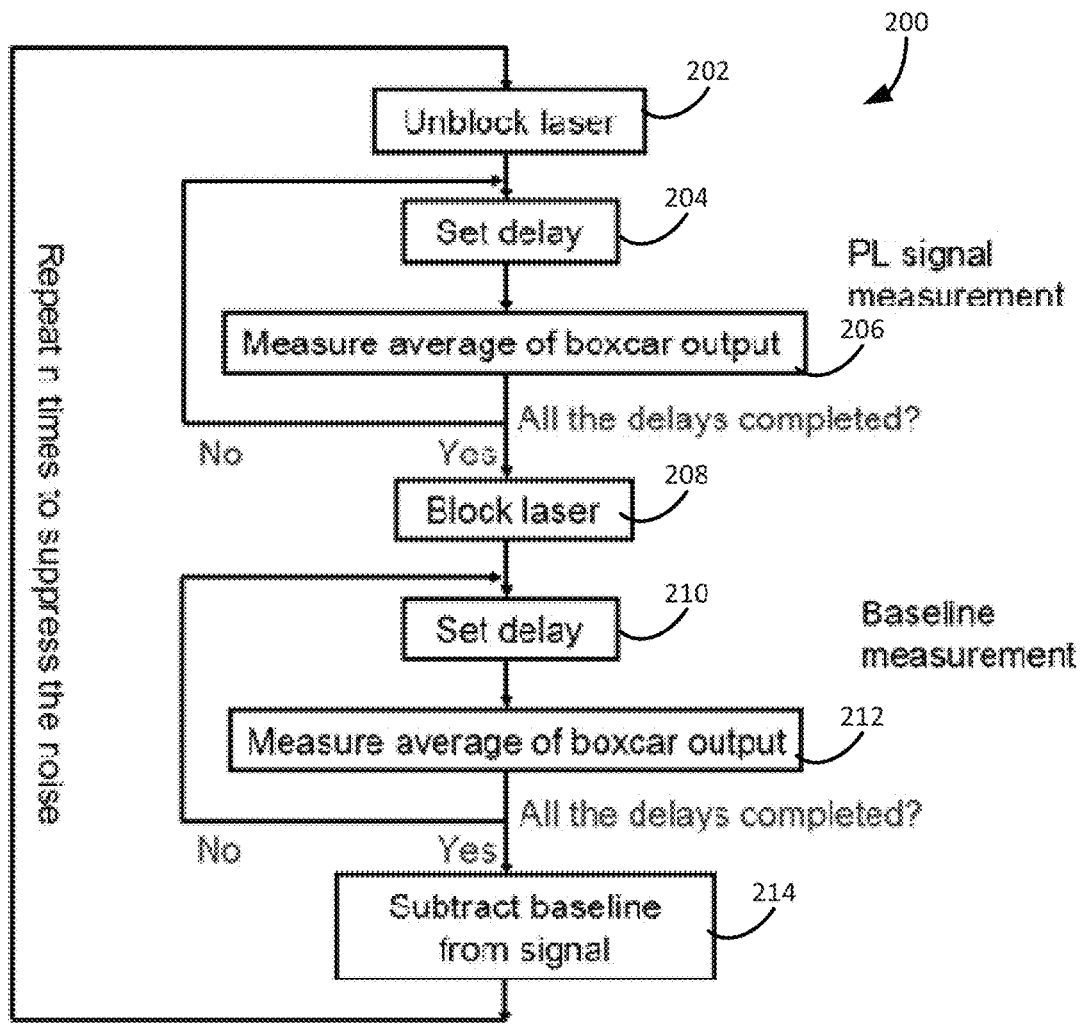
FIG. 2 is a flow chart illustrating the TRPL measurement using the traditional setup of FIG. 1.

The measurement procedure as shown with a flow chart 200 is given in FIG. 2. In particular, in operation 202, the laser 118 is turned on utilizing the laser control box 116 and unblocked to being measuring the PL signal. The computer 102 sets a delay of the boxcar 112 in operation 204. The boxcar 112 measures the voltage value of the PL signal and then gives the value to the computer 102 for data acquisition in operation 206. Next, the system 100 determines if all of the boxcar delays are completed and, if not, the computer 102 sets the boxcar 112 to the next delay and repeats operations 204 and 206. Further, the repeating of these steps may continue until the PL signals at all the delays are measured.

Once the PL signals at all of the delays are measured, the system 100 blocks in the laser in operation 208, sets a delay of the boxcar 112 in operation 210 and measures the average of the boxcar 112 output in operation 212. Similar to above, the system 100 determines if all of the boxcar delays are completed and, if not, the computer 102 sets the boxcar 112 to the next delay and repeats operations 210 and 212. These operations are executed to collect a baseline measurement.

In operation 214, the baseline measured is subtracted from the signal measured in operations 204 and 206 to eliminate the baseline. Each operation of the method 200 is repeated several times so that an average can be taken and used to suppress the noise.

The repeated operations 204 and 206 measures the PL signal, but the non-zero boxcar baseline is mixed in with the PL signal. Therefore, operations 208-212 are generally used to collect the baseline. However, this method works only when the baseline does not drift as a function of time. In a realistic case, the baseline drifts, adding an error bar to the final result. The baseline drift will be discussed in Section 3.1 and Section 3.2.2 below. Further, this method 200 generally also suffers from a large 1/f noise, which will be discussed in Section 3.1 and Section 3.2.1 below. Therefore, a real-time baseline correction method is introduced to reduce these noise sources, and is described in the following section.

2.2 Real-Time Baseline Correction TRPL Setup

A "frame-to-frame subtraction" concept, also known as "real-time baseline correction" concept, is introduced to solve the long-term temperature drift problems in the Fourier transform infrared spectroscopy (FTIR) systems. Due to the similar features of the temperature drift problem in the FTIR system and the baseline drift problem in the TRPL system, a TRPL experimental setup is described herein and shown in FIG. 3. In this new setup 300, the laser is modulated twice, therefore it is named "real-time baseline correction" method. The similarities and differences between the "frame-to-frame subtraction" in FTIR and "real-time baseline correction" in TRPL will be discussed later.

Figure 3:
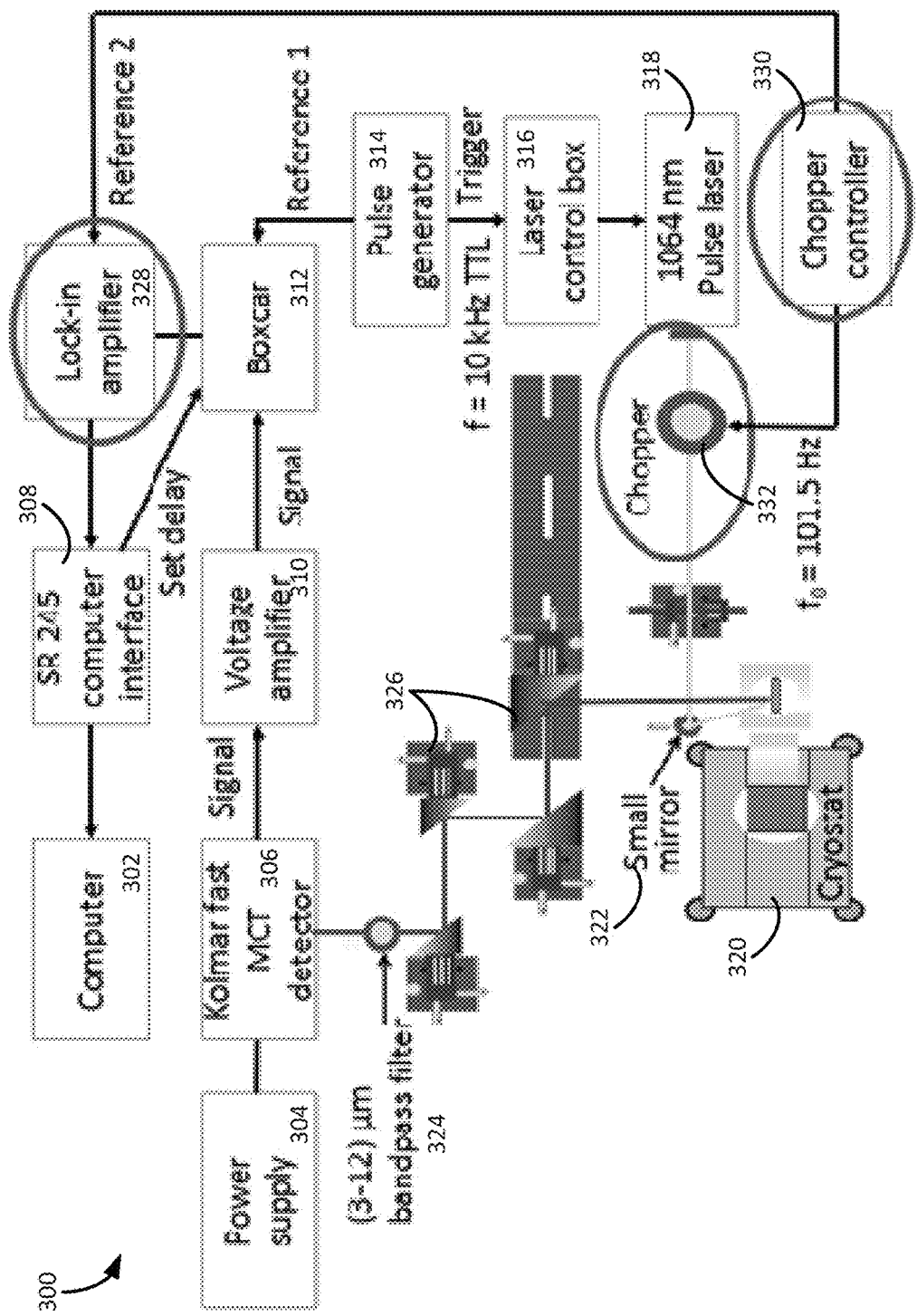
FIG. 3 is a simplified illustration showing a real-time baseline correction TRPL setup.

The modified TRPL setup 300 is shown in FIG. 3. In general, the system 300 includes the same or similar components as the system 100 of FIG. 1 described above. Those components that are the same or similar as those in the above system 100 include a similar numerical designator in FIG. 3. For example, the computer 102 discussed in the system 100 above is the same or similar to the computer 302 of the system 300 of FIG. 3. However, the system 300 of FIG. 3 includes an additional lock-in amplifier 328, a chopper 332, and a chopper controller 330. In general, the modulations of the system 300 can be realized by any electrical or mechanical approach. In the particular case illustrated, a chopper 332 and a lock-in amplifier 328 are added to the system such that the real-time baseline correction is realized by a TTL signal and a chopper. The principle that this real-time baseline correction method suppresses the noise will be discussed in detail in Section 3 below.

Figure 4:
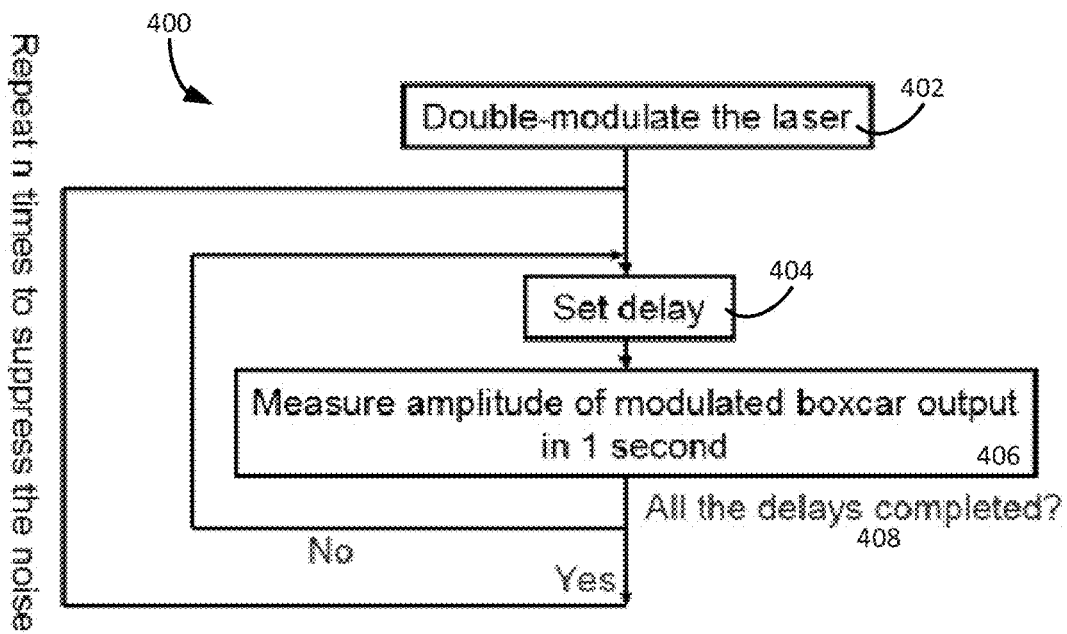
FIG. 4 is a flow chart illustrating the TRPL measurement using the real-time baseline correction setup of FIG. 3.
Figure 5:
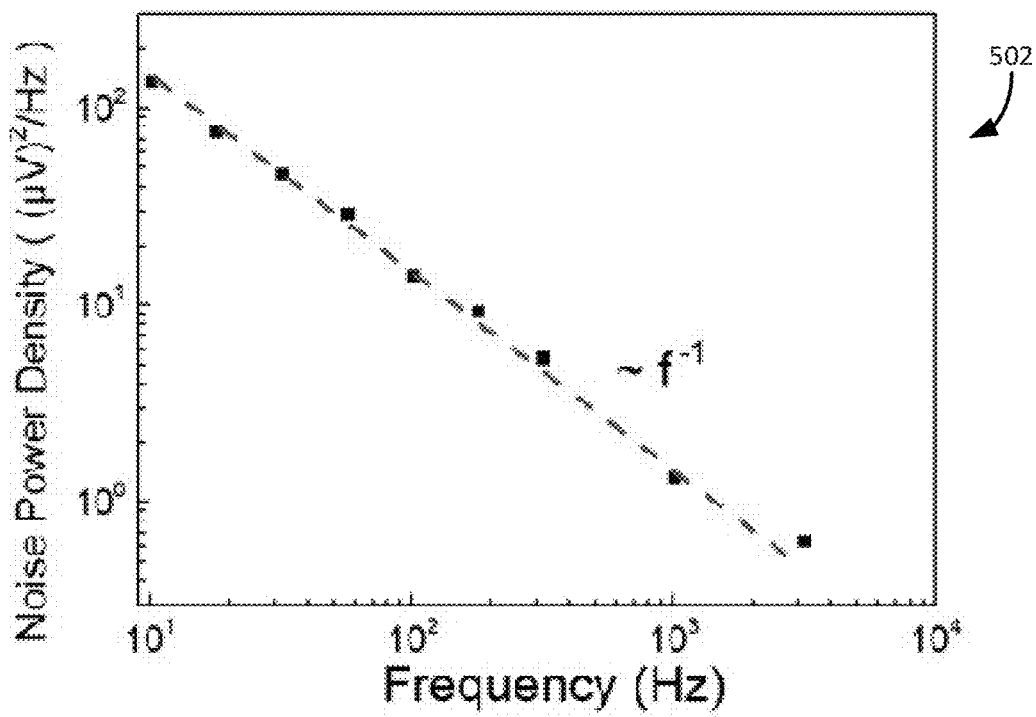
FIG. 5 is a graph of a noise power spectrum in a TRPL experiment measured from a single boxcar output using a Stanford SR 830 lock-in amplifier.

Utilizing the system 300 of FIG. 3, the measurement procedure to obtain the TRPL measurement using the real-time baseline correction is shown in the flow chart of FIG. 4. In particular, the laser 318 is double-modulated in operation 402 by the TTL signal and the chopper 332, where the frequency of the TTL signal is much higher than the frequency of the chopper. In operation 404, the initial delay of the boxcar 312 is set by the computer 302. The boxcar 312 output is measured by a lock-in amplifier with a time constant of 300 ms, synchronized with a chopper 332 in operation 406. After an integration time of 1 second, the lock-in amplifier 328 gives the amplitude of the signal to the computer 302 for data acquisition. The amplitude of the signal is proportional to the PL intensity at this delay. In operation 408, the system 300 determines if all of the delays have been completed and, if not, the computer 302 sets the boxcar 312 to the next delay and repeats operation 406. Further, operations 404 through 408 may be repeated several times to suppress the noise of the measurement.

A comparison between the "frame-to-frame subtraction" in FTIR and the "real-time baseline correction" in TRPL is briefly discussed in this paragraph. Conventionally both FTIR and TRPL experiments have a recurring signal, which is the interferogram in the FTIR experiment and the laser pulse in the TRPL experiment. Both methods add a modulation to the optical signal on the basis of the conventional FTIR and TRPL experiment. The general requirement for a real-time baseline correction is that among the two frequencies, which are the signal recurring frequency and the modulation frequency, one of them is much larger than the other, so that they do not interfere with each other. As will be pointed out later, higher modulation frequencies are better in suppressing the drifting problems. The signal recurring frequency in a conventional FTIR is on the order of kHz, and the "frame-to-frame subtraction" provides a modulation frequency on the order of 50 kHz, much higher than the signal recurring frequency in the conventional FTIR. But in the TRPL experiment, due to the long minority carrier lifetime on the order of tens of microseconds, the modulation frequency has to be much lower than the signal recurring frequency. Table 1 summarizes the similarities and differences.

TABLE 1

The similarities and differences between the "frame-to-frame subtraction" in FTIR and the "real-time baseline correction" in TRPL

|  | "Frame-to-frame subtraction" in FTIR | "Real-time baseline correction" in TRPL |
|---|---|---|
| Similarities | Add a modulation to the conventional experiment | |
| Differences | Modulation frequency much higher than the signal recurring frequency | Modulation frequency much lower than the signal recurring frequency |

3. Noise Analysis and Simulation

Even though the laser can excite the initial excess carrier density up to the order of $10^{18}/cm^3$, infrared detectors typically operate in low optical excitation regimes with photogenerated carrier density lower than $10^{15}/cm^3$. Valuable information about the material properties for infrared detectors can be achieved when the excess carrier density is small enough. Low excess carrier density means low PL intensity per unit area. In an ideal case, assuming a 100% optical collection efficiency, a 100% external quantum efficiency of the sample, and the detector is the only noise source, the lowest photogenerated carrier density that can be resolved is limited by the detectivity of the detector and is estimated to be on the order of $10^{12}/cm^3$ in MWIR InAs/InAsSb T2SLs. In a realistic case, the optical collection efficiency and external quantum efficiency are lower than 100%, and other noise sources are present, so the signal is weaker and noise is stronger than the ideal case. A detector with a larger effective area is desired in order to collect more PL and increase the signal intensity; however larger effective area comes with lower bandwidth. For TRPL of the InAs/InAsSb superlattices, the bandwidth of the detector has to be no less than 50 MHz to have sufficient time resolution, which limits the effective area of the detector, and thus limits the total collected PL signal to be relatively weak. To resolve the PL decay with low intensity, it is required that the noise is suppressed to a level which is significantly lower than the weak PL signal. The conventional TRPL experimental setup uses a traditional method to suppress the noise, which takes the moving average of the obtained data. However, this method is not always the most efficient, depending on the characteristics of the noise. This Section will discuss the dominant noise sources in the TRPL experiment, and demonstrate that the real-time baseline correction method is more efficient in suppressing the noise than the traditional method.

3.1 Noise Identification

First, the 1/f noise is identified to be dominant from 10 Hz to 3 kHz during the experimental measurements. In one embodiment, the noise spectrum is measured using a Stanford SR 830 lock-in amplifier, by manually changing the internal frequency and reading the noise spectral density. The measured noise power spectrum of a single output from the boxcar 312 is illustrated in the graph 502 of FIG. 5. As shown, the total noise of the output of the boxcar 312 is dominated by the 1/f noise from 10 Hz to 3 kHz. This includes the noise from the detector 306, the amplifier 310, the boxcar 312, the laser 318 and the cables, but the noise spectral densities measured at the boxcar output is almost the same as that at the detector output, therefore, it is concluded that the 1/f noise is mainly from the detector.

Figure 6A:
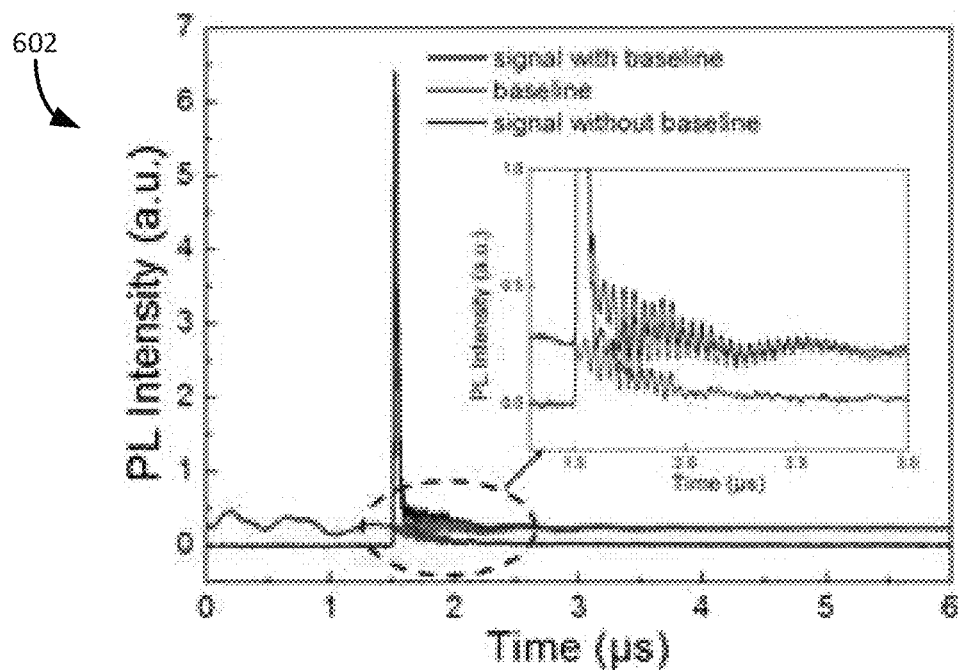
FIGS. 6A and 6B are graphs showing the boxcar baseline fluctuation issue in the traditional method.
Figure 6B:
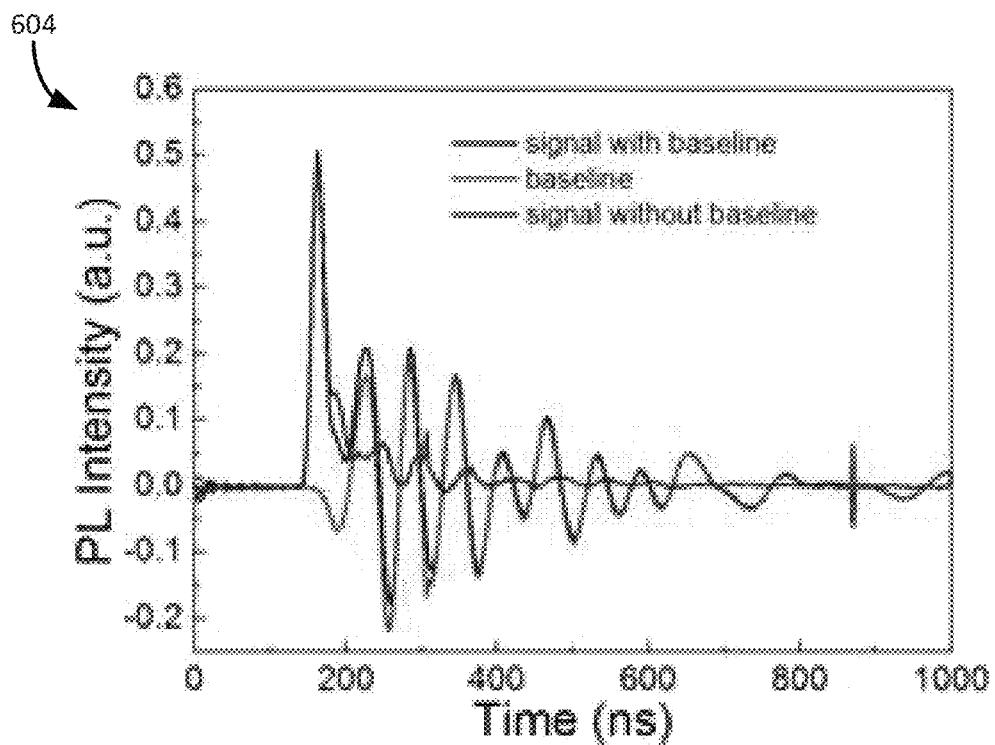
Figure 7:
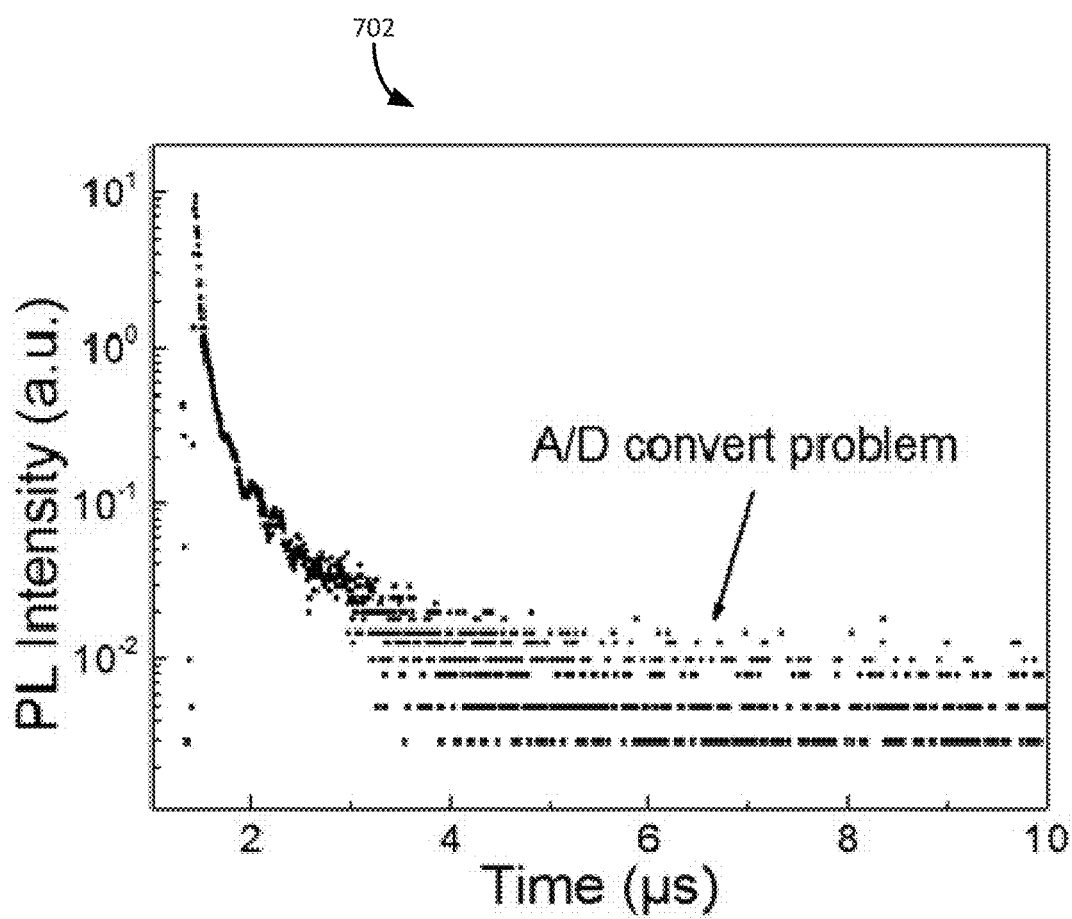
FIG. 7 is a graph showing A/D conversion issue in the traditional method.

Secondly, there is strong sub-Hertz noise associated with boxcar baseline drift. The baseline drift is commonly observed in boxcars, also very common in electrocardiography, chromatography, and infrared detectors. The drift is attributed to all kinds of fluctuations in the system. In the disclosed system, it may be observed that two sources can cause the baseline to oscillate: the trigger signal of the boxcar and the electromagnetic wave coming from the laser. Many factors that change during the experiment can cause the baseline to drift, including the intensity, periodicity, jitter of the trigger pulse, external interfering electromagnetic wave, power line, mechanical vibration, etc. The measuring procedures of the traditional TRPL experiment are designed to get rid of the boxcar baseline, by assuming the baseline does not change from measurement to measurement. However the laser block/unblock frequency is on the order of (0.1~1) Hz, and the baseline will have changed when switching between the signal measurement and the baseline measurement over such a time scale. Therefore, simply subtracting the baseline cannot fully cancel it, as can be seen in the graphs of FIGS. 6A and 6B, in the experiments with the traditional method, the subtracted signal does not fully eliminate the baseline. The sample 602 in FIG. 6A has a stronger PL signal, but we can still see some features of the baseline fluctuation mixed with the PL decay in the subtracted signal. On the other hand, for samples with a weaker PL signal (graph 604 of FIG. 6B), the signal after subtraction is still overwhelmed by the baseline fluctuations.

Further, digitization of the signal may also be addressed. As previously discussed, low excess carrier density gives more information for infrared materials. This requires that a signal has a dynamic range of at least 3 to 4 orders of magnitude. However, the traditional TRPL setup is not capable of that dynamic range due to the A/D converter. The Stanford SR 245 computer interface has a resolution of 2.5 mV and the maximum output of the boxcar is 10 V, therefore they have a dynamic range of 4000. If the signal has a dynamic range larger than or close to 4000, while keeping the boxcar from overloading, the information at low intensities will be lost. As shown in graph 702 of FIG. 7, the signal between 4 μs and 10 μs are digitized.

3.2 Method Analysis

As analyzed previously, the main problem of the traditional TRPL setup is the 1/f noise and the baseline drift issue, both of which are low frequency noise. One way to get rid of the low frequency noise is by modifying the impulse response function of the system so that it is less affected by the low frequency noise. Real-time baseline correction is a method that can modify the impulse response function. As discussed in Section 2.2, in this specific case, the real-time baseline correction is realized by double-modulating the laser with the TTL signal and the chopper, and collecting the signal with a lock-in amplifier.

3.2.1 Suppressing the 1/f Noise

The 1/f noise is significantly suppressed by the impulse response function of the real-time baseline correction method compared with the traditional method.

To understand what happens to the noise in the frequency domain in this experiment, it is worth noting that in the real-time baseline correction method, the process that measures the signal from the boxcar output using a lock-in amplifier is equivalent to the following procedures in the time domain:

1. Multiply the boxcar output by a sin wave with a modulation frequency $f_0$
2. Convolve with a square pulse which has a width of 1 second
3. Multiply a periodic delta function with a period of 1 second
4. Convolve with a square pulse with a width of 1 second again Accordingly, in the frequency domain it follows the procedures:

1. Convolve the spectrum of the boxcar output with a double delta function at $\pm f_0$
2. Multiply the spectrum of the 1 second pulse, which is close to constant when 0<f<1 Hz, and its envelope decays to 1/f when f>1 Hz
3. Convolve with a periodic delta function whose period is 1 Hz, which gives a periodic extension of the previous spectrum
4. Again multiply the spectrum of the 1 second pulse For 1/f noise, step 1 determines that the value of the spectrum near 0 Hz achieved in this step is close to the value in the spectrum of the boxcar output near $f_0$. Then step 2 smears out the spectrum higher than 1 Hz. After step 3 of periodic extension, the spectrum has a flat envelope at all frequencies, and the value is determined by the value near 0 Hz in the spectrum achieved by step 2. After step 4 the shape of the final spectrum is close to the spectrum of the 1 second pulse, and the intensity is determined by the intensity in the spectrum achieved in step 3, which is determined by the spectral density at DC in the result of step 2, and eventually it is determined by the noise spectral density in the original noise spectrum at f0. As a comparison, the traditional method also equivalently has 4 steps: it does the same in step 2 to step 4, but in step 1 it has much lower frequency, close to DC. The noise intensity is then determined by the noise spectral density in the original noise spectrum at DC.

The conclusion is, the noise in the result of the real-time baseline correction method is proportional to the noise spectral density in the original noise spectrum at f0. For the dominant 1/f noise in this experiment, the noise spectral density at f0 is lower than that at DC frequency. Therefore, the real-time baseline correction can suppress the noise more efficiently than the traditional method.

3.2.2 Minimizing the Baseline Drift

The reason why the real-time baseline correction method can suppress the baseline drift noise is shown in the graphs of FIGS. 8A through 8D2. These graphs compare how the real-time baseline correction setup measures the detector output at a fixed delay to the traditional setup. When the laser is unblocked, the detector receives the PL signal and gives an output, as shown in graph 802 of FIG. 8A. For the same delay, the traditional method measures the signal and measures the baseline. Graph 804 of FIG. 8B1 shows these processes, in the first half of time the laser is unblocked and in the second half of time the laser is blocked. However, the repeated steps to obtain the baseline are not performed immediately, instead there is a time gap between them on the order of (1~10) seconds, which corresponds to (0.1~1) Hz, so as to complete all the delays for the signal measurement. In a realistic measurement, there is a low frequency drift of the baseline as discussed in Section 3.1, which introduces a big difference between the baselines measured, as shown in graph 808 of FIG. 8C1. As a comparison, the real-time baseline correction method modulates the laser at a frequency much higher than the traditional method, the detector output after modulation is shown in graph 806 of FIG. 8B2. In this method, the laser block/unblock frequency is much higher than the traditional method, therefore the baseline drift is much smaller than the traditional method, as shown in graph 810 of FIG. 8C2. The boxcar output is the baseline plus the signal, which is shown in graph 812 of FIG. 8D1 and graph 814 of FIG. 8D2 for the traditional method and the real-time baseline correction method, respectively. Since the baseline drift is minimized, the peak to peak value in the boxcar output given by the real-time baseline correction method is less affected by the baseline drift in graph 814. In comparison, as a result of baseline drift, the result achieved by the traditional method, which is the difference between the averaged boxcar output values of the first and second half of time, have a larger deviation from the signal (graph 812).

As discussed, FIGS. 8A-8D2 show a comparison between the signals in the traditional method (1) and the real-time baseline correction method (2). FIG. 8A shows the detector output when the laser is unblocked. When the traditional method works, the block/unblock procedure makes a detector signal like FIG. 8B1. When the real-time baseline correction method works, the modulated detector output is like FIG. 8B2. FIG. 8C1 shows the boxcar baseline drift in the traditional method due to a time gap, and the baseline of the real-time baseline correction method in FIG. 8C2 shows a reduced drift. The output signal from the boxcar is shown in FIG. 8D1 as achieved by the traditional method and FIG. 8D2 as achieved by the real-time baseline correction method.

3.2.3 Improving the A/D Conversion

In addition, the real-time baseline correction method can also solve the A/D conversion resolution issue by measuring the signal of different intensities using different sensitivity scale of the lock-in amplifier. The signal can be clearly taken at different dynamic ranges while the boxcar will not be overloaded.

3.3 Noise Simulation

To examine its effectiveness, the TRPL measurement using this real-time baseline correction method is simulated using Matlab. In a real experiment, when the delay of the boxcar is fixed, the boxcar output is a fixed voltage mixed with noise. The Matlab program simulates a measurement of the fixed voltage. Both traditional and real-time baseline correction methods are simulated. In the simulations, the signal is a voltage of 1 V. The sampling rate is $10^4$ Hz, the modulation frequency is $10^2$ Hz, and a single measurement takes 1 second. Accordingly, the Matlab program generates $10^4$ data points to mimic a single measurement in 1 second. The single measurement is repeated $10^3$ times to identify how the noise is suppressed by each method.

Considering the self time-correlation of the noise, the sequence of the noise has to be kept in order to restore the condition in a real experiment. In the real-time baseline correction method, since the measurement at a fixed delay is done continuously, the noise array is generated directly with a size of $10^4 \times 10^3 = 10^7$. In the traditional method, there is a time gap between the baseline and signal measurements at that delay. Assuming there are $10^2$ delays to measure, and the boxcar gives a moving average of 50 data points. In such a case a full scan of all the delays has $5 \times 10^3$ data points, in which only $5 \times 10^1$ is measuring at that delay. Therefore, a temporary noise array is first generated as $10^7 \times 10^2 = 10^9$ data points, then the first $5 \times 10^1$ of every $5 \times 10^3$ data point grouping are extracted to form a new noise array with a total size of $10^7$, which will be used for the simulation. Three different types of noise are generated for comparison. A white noise is generated by randomly generating $10^7$ data of normal distribution. A 1/f noise is generated by generating a white noise, performing a Fourier transform and multiplying by $1/f^{1/2}$, then calculating the reverse Fourier transform, where f is the frequency. A "blue" noise is generated by generating a white noise, doing Fourier transform and multiplying by $f^{1/2}$, then determining the reverse Fourier transform. All three types of noise have a mean value of 0, which is easy to demonstrate numerically.

The simulation of the traditional method follows the procedures:

1. Generate a noise array using the above approach (called "array of noise" in the following text) with a size of $10^7$.
2. Divide the noise array into $10^3$ sub-arrays, so that each of them has a size of $10^4$.
3. Select the first sub-arrays.
4. Add the signal to every other 50 data points of the sub-array.
5. Calculate the average of the data points that contains the signal, then minus the average of the data points that do not contain the signal. The difference is the measured result.
6. Select the next sub-array.
7. Repeat step 4 to step 6 for the sub-arrays in sequence, until all the $10^3$ sub-arrays are handled. Record all the measured results.
8. Plot the measured results and calculate the variance.

The simulation of the real-time baseline correction method follows the procedures:

1. Generate an array of noise with a size of $10^7$.
2. Divide the noise array into $10^3$ sub-arrays, so that each of them have a size of $10^4$.
3. Select the first sub-array.
4. Add the actual signal to every other 50 data points of the sub-array, and get a new sub-array named sub-array-1.
5. Multiply the sub-array-1 with a sin wave starts with a phase of 0, and get a new sub-array named sub-array-2.
6. The average value of the $10^4$ data points in sub-array-2 multiplied by $\pi$ is the measured result.
7. Select the next sub-array.
8. Repeat step 4 to step 7 for the sub-arrays in sequence, until all the $10^3$ sub-arrays are handled. Record all the measured results.
9. Plot the measured results and calculate the variance.

Step 4 simulates the modulation process. Step 5 and 6 simulates a lock-in amplifier to collect the signal with a proper phase.

Figure 9A:
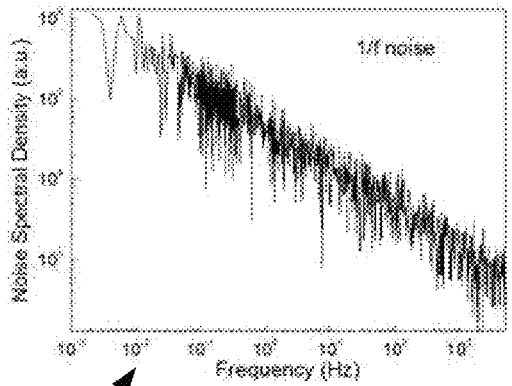
FIGS. 9A-9F are graphs showing a comparison between the simulation results of the traditional method and the real-time baseline correction method for a modulation frequency $f_0$=100 Hz, and an integration time of 1 second for a single measurement.
Figure 9B:
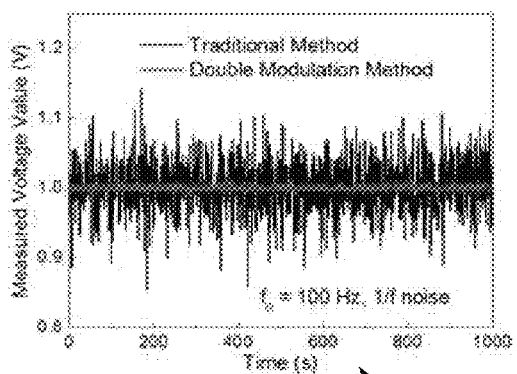
Figure 9C:
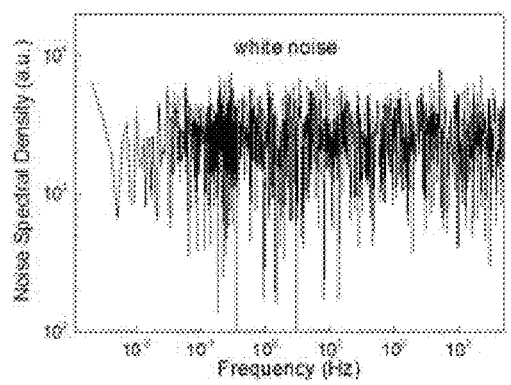
Figure 9D:
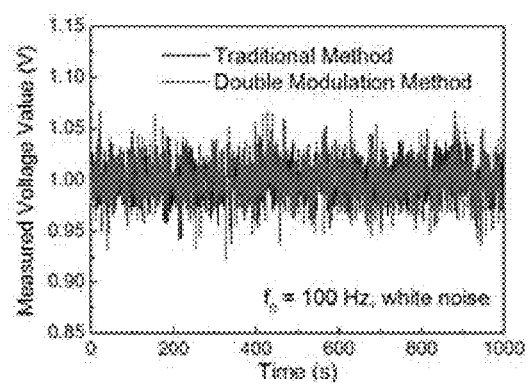
Figure 9E:
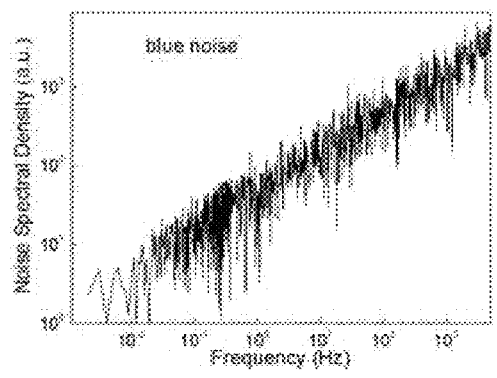
Figure 9F:
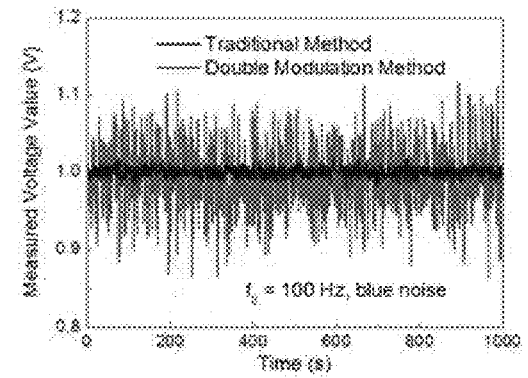

The simulation results are shown in the graphs of FIGS. 9A through 9F and the variance of these results are shown in Table 2. For 1/f noise, which is more significant at low frequencies than high frequencies (graph 902 of FIG. 9A), the real-time baseline correction method significantly reduces the variance of the measurement results compared with the traditional method (graph 904 of FIG. 9B), by an order of 2 (Table 2). For white noise which has an even weight at all frequencies (graph 906 of FIG. 9C), both methods behave similarly (graph 908 of FIG. 9D). For blue noise which has more weight at high frequencies (graph 910 FIG. 9E), the real-time baseline correction method has larger variance than the traditional method (graph 912 of FIG. 9F), by an order of 2. It is shown previously that the noise is proportional to the noise spectral density at the modulation frequency, thus the variance is proportional to the noise power density at the modulation frequency. For the real-time baseline correction method, the modulation frequency in this case is 100 Hz, and for the traditional method, the modulation frequency in this case is equivalently 1 Hz. For the 1/f noise, the noise power density at 100 Hz is 2 orders lower than that at 1 Hz, so the variance of the real-time baseline correction method is 2 orders lower than the traditional method. For the white noise, the noise power density at 100 Hz is the same as that at 1 Hz, so both methods show similar variance. For the blue noise, the noise power density at 100 Hz is 2 orders larger than that at 1 Hz, so the variance of real-time baseline correction method is 2 orders larger than the traditional method. These are in consistent with the simulation results. FIG. 9B shows that the 1/f noise can be reduced by the real-time baseline correction technique significantly more efficiently than the traditional method.

The graphs of FIGS. 9A through 9F shows a comparison between the simulation results of the traditional method and the real-time baseline correction method for a modulation frequency $f_0$=100 Hz, and an integration time of 1 second for a single measurement. The results achieved in FIGS. 9B, 9D and 9F, use FIG. 9A-1/f noise, FIG. 9C-white noise and FIG. 9E-blue noise, respectively.

TABLE 2

Comparison between the variance of the simulation results achieved by the traditional method and the real-time baseline correction method with a modulation frequency of 100 Hz and different types of noise

| Type of noise | 1/f noise | White noise | Blue noise |
|---|---|---|---|
| Frequency dependence of the noise power density | $f^{-1}$ | $f^0$ | $f^1$ |
| $\dfrac{\sigma^2_{Traditional}}{\sigma^2_{RBC}} \quad \dfrac{\sigma^2_{Traditional}}{\sigma^2_{Double-Modulation}}$ | $1.03 \times 10^2$ | $0.98 \times 10^0$ | $1.05 \times 10^{-2}$ |

To show how the modulation frequency affects the noise in the real-time baseline correction method, different modulation frequencies are used in the simulation with the 1/f noise. From the graphs illustrated in FIGS. 10A through 10C it can be seen that at higher frequencies the noise is reduced more efficiently. In Table 3, it shows that the ratio between the variance achieved in these two methods is proportional to the modulation frequency. For 1/f noise, the noise power density is proportional to 1/f, and it was previously shown that the variance is proportional to the noise power density at modulation frequency, so the ratio between the variance is predicted to be proportional to the modulation frequency. Therefore, the simulation result agrees with the analysis in Section 3.

Figure 10A:
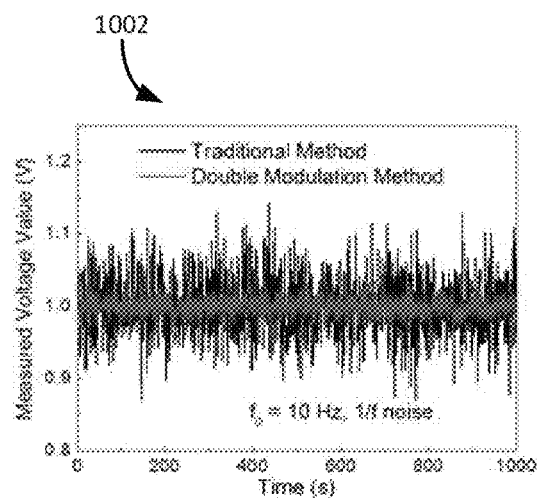
FIGS. 10A-10C are graphs showing a comparison between the simulation results of the real-time baseline correction method and the traditional method with modulation frequencies of 10 Hz, 100 Hz and 1000 Hz, respectively'
Figure 10B:
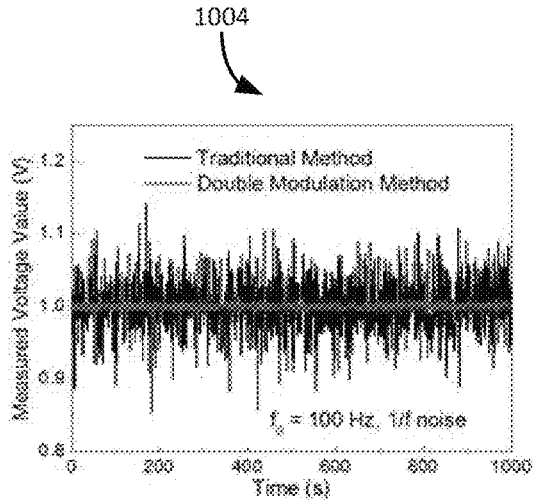
Figure 10C:
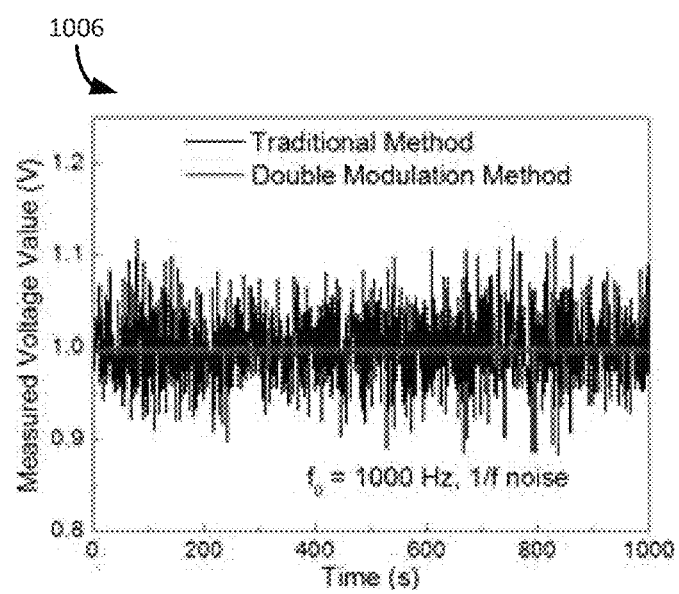

FIGS. 10A-C show a comparison between the simulation results of the real-time baseline correction method and the traditional method, with modulation frequencies $f_0$ of graph 1002 at 10 Hz, graph 1004 at 100 Hz and graph 1006 at 1000 Hz.

Table 3 shows a comparison between the variance in the simulated results achieved by the traditional method and the real-time baseline correction method, with different modulation frequencies using 1/f noise.

TABLE 3

Comparison between the variance in the simulated results achieved by the traditional method and the real-time baseline correction method, with different modulation frequencies using 1/f noise.

| Modulation frequency (Hz) | 10 | 100 | 1000 |
|---|---|---|---|
| $\dfrac{\sigma^2_{Traditional}}{\sigma^2_{RBC}}$ $\dfrac{\sigma^2_{Traditional}}{\sigma^2_{Double-Modulation}}$ | $1.07 \times 10^1$ | $1.03 \times 10^2$ | $1.02 \times 10^3$ |

To mimic the real TRPL measurement by these two methods over the same period of time more closely, the measurement of a voltage which decays single exponentially in $10^3$ seconds is simulated. Two types of noise are chosen, which are 1/f noise (shown in graph 1102 of FIG. 11A, to mimic the 1/f noise in the experiment) and a lower frequency noise (~f–6, shown in graph 1106 of FIG. 11C, to mimic the sub-Hertz noise in the experiment). In this case, the noise arrays for both methods are generated directly with a size of $10^7$.

The simulation of the traditional method uses the following procedure:

1. Generate an array of noise with a size of $10^7$.
2. Take the first $10^5$ data points, divide them into $2\times10^3$ groups. Each group has a size of 50 and represents the 50 data points taken by the boxcar for the moving average at each delay. The first $10^3$ groups will be the signal measurement and the second $10^3$ groups will be the baseline measurement.

3. Calculate the signal at different delays as signal= $A \times e^{-B \times delay}$.
4. Add the signal to the first $10^3$ groups.
5. Calculate the average of the 50 data points in each group, and achieve an array with a size of $10^3$ as the signal measurement result, and another array with a size of $10^3$ as the baseline measurement result.
6. Subtract the baseline from the signal, name the result as "the corrected signal array".
7. Take the next $10^5$ data points.
8. Repeat step 4 to step 7 for 100 times, then calculate the average of all the corrected signal arrays, which is the measurement result.
9. Plot the result.

The simulation of the real-time baseline correction method follows the procedures:
1. Generate an array of noise with a size of $10^7$.
2. Divide them into $10^3$ sets. Each set has a size of $10^4$ and represents the data that are used for the measurement at each delay.
3. Calculate the signal at different delays as signal= $A \times e^{-B \times delay}$.
4. Take the first set.
5. Add the signal that corresponds to this set to every other 50 data points in the set.
6. Generate a sin wave with a peak to peak value of 2, and the same frequency as the modulation frequency, with a starting phase of 0. Multiply the sin wave with the data in the set. This step generates a new array with a size of $10^4$ for the set.
7. Calculate the average of the $10^4$ data points, and then multiply it by $\pi$. The result is the measured signal at this delay.
8. Take the next set.
9. Repeat step 5 to step 8 until all the sets are handled.
10. Plot the simulation result.

Step 4 or step 8 mimics choosing a delay in a real experiment. Step 5 mimics the modulation process. Step 6 and step 7 mimics the measurement using a lock-in amplifier with proper phase.

FIGS. 11A-11D show the simulation results. When the noise is dominated by 1/f noise shown in graph 1102, the real-time baseline correction method gives a clearer result than the traditional method, shown in graph 1104. For the lower frequency noise shown in graph 1106, the result in graph 1108 shows a slow variation by the traditional method, which makes the decay tail very different from the single exponent. As a comparison, the real-time baseline correction is much more robust and gives a much clearer single exponent. Such a result suggests that the 1/f noise and the sub-Hertz baseline noise can be suppress by the real-time baseline correction method more efficiently.

Figure 11A:
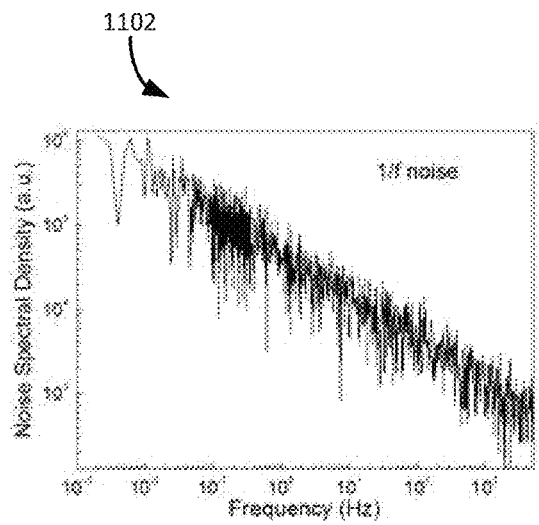
FIGS. 11A-11D are graphs showing a simulation of a real TRPL measurement in a comparison between the real-time baseline correction method and the traditional method.
Figure 11B:
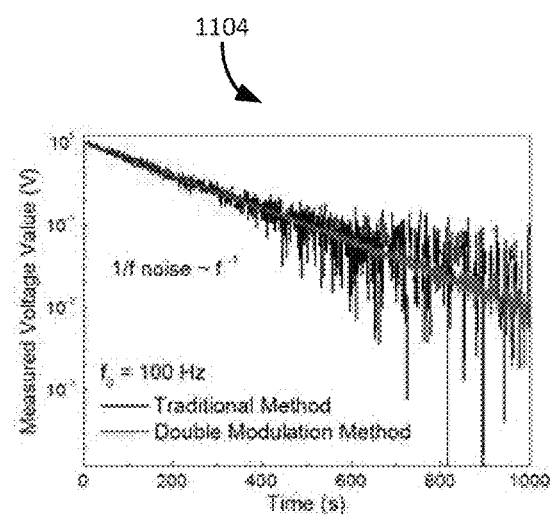
Figure 11C:
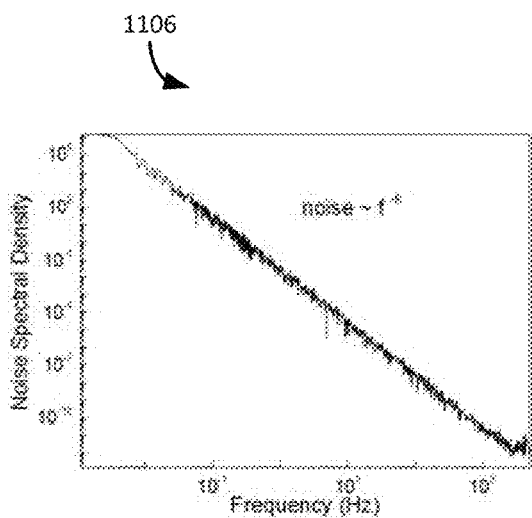
Figure 11D:
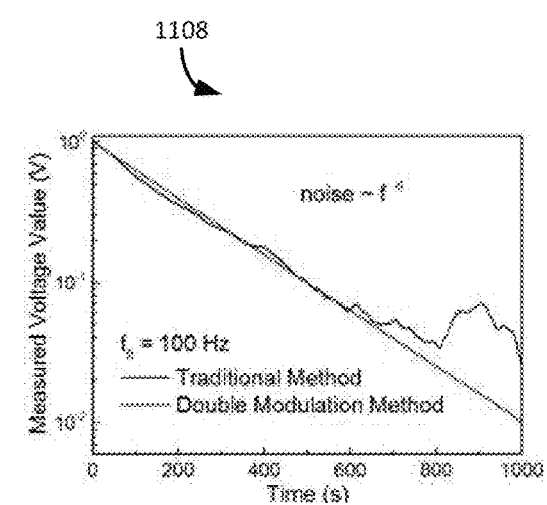

FIGS. 11A-11D show a simulation of a real TRPL measurement, assuming the PL decay is a single exponential; comparison between the real-time baseline correction method and the traditional method. With a 1/f noise shown in FIG. 11A, the simulated result is shown in FIG. 11B. With a noise ~f−6 shown in FIG. 11C, the simulated result is shown in FIG. 11D. The modulation frequency $f_0$=100 Hz.

To summarize Section 3.3, the modeling result suggests that the noise achieved by the real-time baseline correction technique is proportional to the noise spectral density at the modulation frequency in the noise spectrum of the original signal, which agrees with the analysis in Section 3.2.1. As a result, low frequency noises, including the 1/f noise and the baseline drift noise, can be suppressed more efficiently by the real-time baseline correction technique than by the traditional method.

4. Experimental Results

Figure 12:
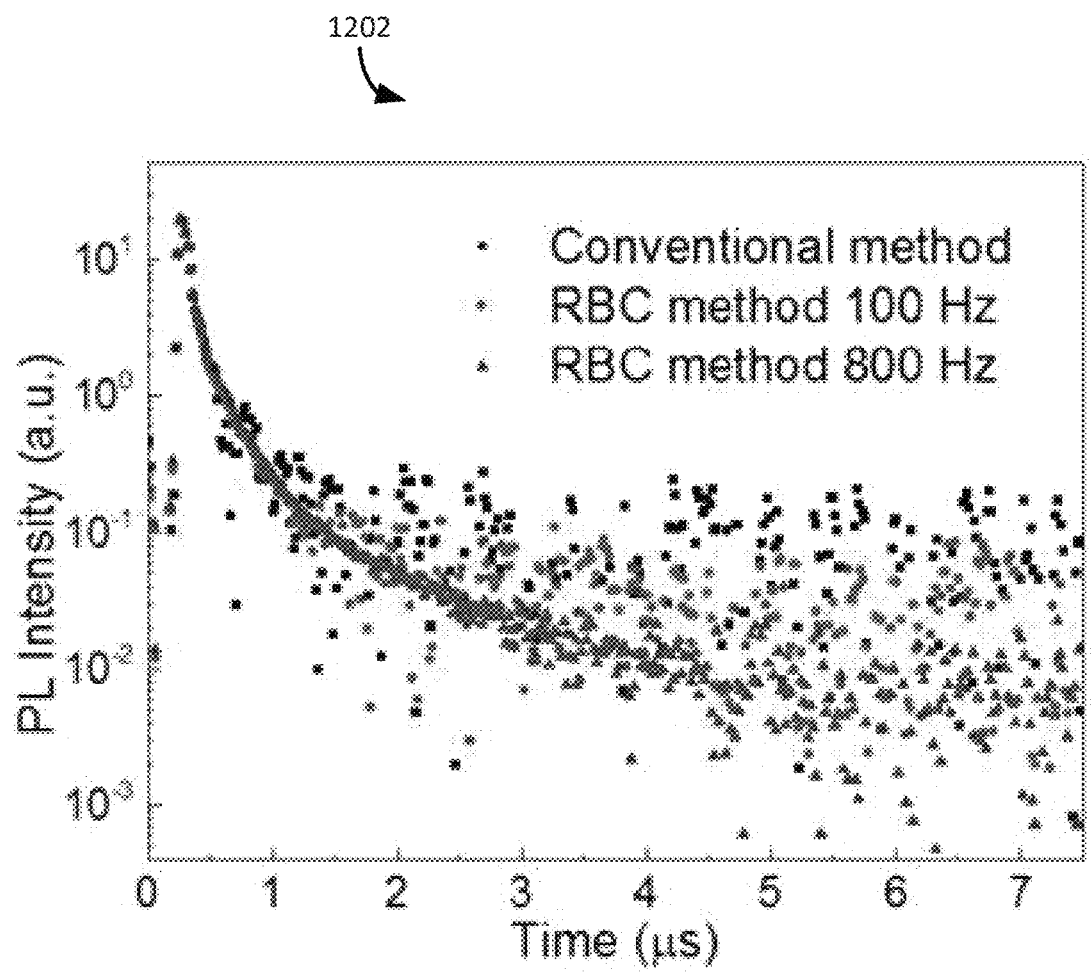
FIG. 12 is a graph showing the real-time baseline correction method removing the noise issues which appear in the traditional method.

A comparison of the experimental results measured using the traditional method and the RBC method with different modulation frequencies, on the same sample, over the same amount of time, is shown in graph 1202 of FIG. 12. From 0.5 µs to 1 µs, the result measured by the traditional method shows multiple oscillations, which are due to the low frequency baseline fluctuation coming from the laser pulse. The RBC method completely removes such oscillations. Noise dominates the tail parts of these decay curves after 5 µs. Compared with the traditional method, the RBC method with a modulation frequency of 100 Hz suppresses the noise by an order of magnitude, while the RBC method with a modulation frequency of 800 Hz suppresses the noise by another order of magnitude, thus resolving the TRPL decay from 1.5 µs to 4.5 µs, which is buried in the noise of the traditional method. This improvement resolves decay features with low PL intensity, in less time, making it more efficient for the TRPL measurements of infrared samples.

The noise issues in a conventional TRPL system using a traditional method, which calculates the average of multiply measurements is analyzed and is determined to be dominated by low frequency noise. Modeling results suggest that a real-time baseline correction method will be more efficient in suppressing such low frequency noise. The real-time baseline correction method can be realized by any types of electrical or mechanical modulations. In this particular case, it is realized by modifying the old TRPL system with a chopper and a lock-in amplifier, and is applied to measure the TRPL of InAs/InAsSb T2SLs. Experimental results demonstrate that the real-time baseline correction method efficiently reduces the noise by suppressing the 1/f noise, removing the baseline fluctuation, and solving the A/D conversion issue, which are the dominant noise sources in the traditional TRPL experiment. After this improvement, the signal-to-noise ratio is significantly enhanced, and the PL decay from lower excess carrier densities, which can give more information but was previously buried in the noise of the traditional method, can be resolved using the real-time baseline correction method in less time.

Figure 13:
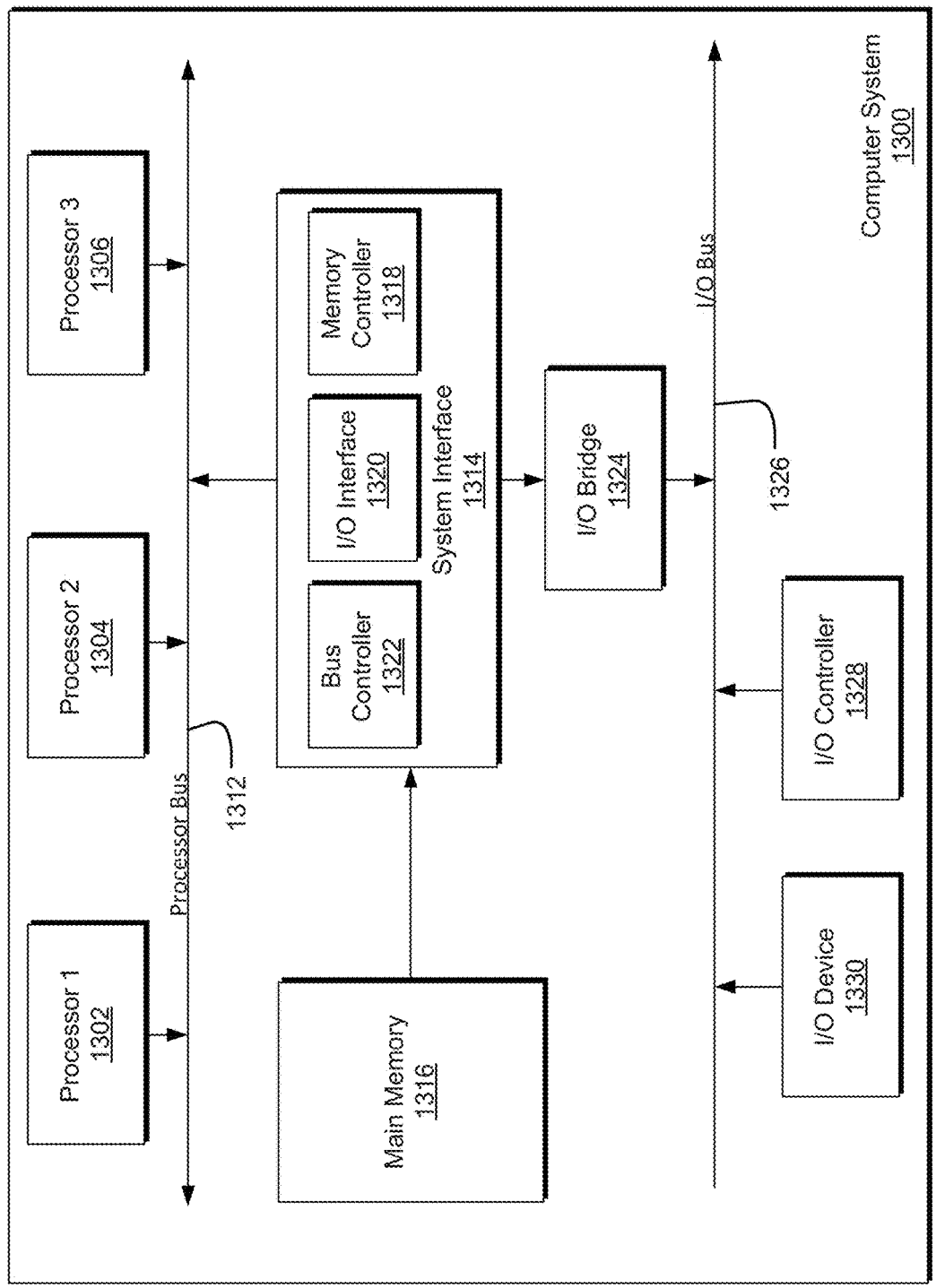
FIG. 13 is a block diagram illustrating an example of a computing device or computer system which may be used in implementing embodiments of the present invention.

FIG. 13 is a block diagram illustrating an example of a computing device or computer system 1300 which may be used in implementing embodiments of the present invention. For example, the computing system 1300 may be the computer 102, 302 described above. The computer system (system) includes one or more processors 1302-1306. Processors 1302-1306 may include one or more internal levels of cache (not shown) and a bus controller or bus interface unit to direct interaction with the processor bus 1312. Processor bus 1312, also known as the host bus or the front side bus, may be used to couple the processors 1302-1306 with the system interface 1314. Processors 1302-1306 may also be purpose built for processing/mixing media data, such as audio or video components of a media stream, such as a digital signal processor. System interface 1314 may be connected to the processor bus 1312 to interface other components of the system 1300 with the processor bus 1312. For example, system interface 1314 may include a memory controller 1318 for interfacing a main memory 1316 with the processor bus 1312. The main memory 1316 typically includes one or more memory cards and a control circuit (not shown). System interface 1314 may also include an input/output (I/O) interface 1320 to interface one or more I/O bridges or I/O devices with the processor bus 1312. One or more I/O controllers and/or I/O devices may be connected with the I/O bus 1326, such as I/O controller 1328 and I/O device 1330, as illustrated.

I/O device 1330 may also include an input device (not shown), such as an alphanumeric input device, including alphanumeric and other keys for communicating information and/or command selections to the processors 1302-1306. Another type of user input device includes cursor control, such as a mouse, a trackball, or cursor direction keys for communicating direction information and command selections to the processors 1302-1306 and for controlling cursor movement on the display device.

System 1300 may include a dynamic storage device, referred to as main memory 1316, or a random access memory (RAM) or other computer-readable devices coupled to the processor bus 1312 for storing information and instructions to be executed by the processors 1302-1306. Main memory 1316 also may be used for storing temporary variables or other intermediate information during execution of instructions by the processors 1302-1306. System 1300 may include a read only memory (ROM) and/or other static storage device coupled to the processor bus 1312 for storing static information and instructions for the processors 1302-1306. The system set forth in FIG. 13 is but one possible example of a computer system that may employ or be configured in accordance with aspects of the present disclosure.

According to one embodiment, the above techniques may be performed by computer system 1300 in response to processor 1304 executing one or more sequences of one or more instructions contained in main memory 1316. These instructions may be read into main memory 1316 from another machine-readable medium, such as a storage device. Execution of the sequences of instructions contained in main memory 1316 may cause processors 1302-1306 to perform the process steps described herein. In alternative embodiments, circuitry may be used in place of or in combination with the software instructions. Thus, embodiments of the present disclosure may include both hardware and software components.

A machine readable medium includes any mechanism for storing information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 1316. Common forms of machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A system for real-time baseline correction of infrared time-resolved photoluminescence comprising:
    a pulse laser device producing a pulsed laser signal to excite a semiconductor device;
    a boxcar integrator receiving the pulsed laser signal from a detector, the boxcar integrator configured to integrate the received pulsed laser signal over a specified gate width following an applied trigger delay, wherein the boxcar integrator receives a square wave signal input to be synchronized with the pulsed laser signal; and
    a chopper device in electrical communication with a chopper device controller to periodically interrupt the pulsed laser signal; and
    a lock-in amplifier configured to receive an output of the boxcar device and the chopper device controller to synchronize the output of the boxcar integrator with the operating frequency of the chopper device to double-modulate the pulsed laser signal by the square wave single input and the operating frequency of the chopper device,
    wherein a frequency of the square wave signal input is higher than an operating frequency of the chopper device.

2. The system of claim 1 further comprising:
    a computing device configured to determine the trigger delay and transmit the trigger delay to the boxcar integrator.

3. The system of claim 2 wherein the lock-in amplifier transmits the synchronized output from the boxcar integrator to the computing device after a designated integration time.

4. The system of claim 3 wherein the designated integration time is 1 second.

5. The system of claim 1 wherein the lock-in amplifier comprises a time constant value of 300 ms.

6. The system of claim 1 wherein:
    the detector receives the pulsed laser signal and provides the pulsed laser signal to the boxcar integrator.

7. The system of claim 6 further comprising:
    a voltage amplifier in communication with the detector for amplifying the received pulsed laser signal prior to providing the pulsed laser signal to the boxcar integrator.

8. The system of claim 1 further comprising:
    a pulse wave generator to create the square wave signal input and transmit the square wave signal input to the boxcar integrator.

9. The system of claim 1 wherein the pulse laser device comprises a 1064 nm pulse laser.

10. A method for real-time baseline correction of infrared time-resolved photoluminescence comprising:
    (a) double-modulating a laser using a transistor-to-transistor logic signal from a pulse generator and a chopper device controller of a chopper device, wherein a frequency of the transistor-to-transistor logic signal is higher than an operating frequency of the chopper device;
(b) setting an initial delay of a boxcar integrator;
(c) measuring an output of the boxcar integrator utilizing a lock-in amplifier while working at the operating frequency of the chopper device to generate an output of the lock-in amplifier, including implementing a predetermined integration time sufficient to make the output of the lock-in amplifier stable;
(d) transmitting the output of the lock-in amplifier to a computer for data acquisition;
(e) setting the boxcar integrator to a next delay;
(f) repeating steps (c) through (e) until a waveform or decay associated with the photoluminescence at a plurality of delays is measured; and
(g) repeating steps (b) through (f) and generating an average of the waveform or decay measured in each cycle to further suppress noise in a photoluminescence signal.

11. The method of claim 10 wherein the chopper device controller is operative to control the chopper device to periodically interrupt a pulsed laser signal.

12. The method of claim 10 wherein the initial delay of the boxcar integrator is set by the computer.

13. The method of claim 10, wherein the chopper device controller is in operative association with the chopper device and the lock-in amplifier.

14. The method of claim 10, wherein the chopper device is in operative association with a pulse laser.

15. The method of claim 14, wherein the pulse laser comprises a 1064 nm pulse laser.

16. The method of claim 10, wherein the amplitude of the transistor-to-transistor logic signal by the lock-in amplifier is sent to the computer for data acquisition after a designated integration time.

17. The method of claim 16 wherein the designated integration time is 1 second.

18. The method of claim 10 wherein the boxcar integrator is configured to integrate the double-modulated laser over a specified gate width following initial delay.

19. The method of claim 18 wherein the specified gate width is 300 ms.

* * * * *